United States Patent [19]

Ornstein

[11] Patent Number: 4,902,695

[45] Date of Patent: Feb. 20, 1990

[54] EXCITATORY AMINO ACID RECEPTOR ANTAGONISTS

[75] Inventor: Paul L. Ornstein, Indianapolis, Ind.

[73] Assignee: Eli Lilly and Company, Indianapolis, Ind.

[21] Appl. No.: 309,562

[22] Filed: Feb. 13, 1989

[51] Int. Cl.$^4$ .................... A61K 31/47; C07D 215/14; C07D 215/36

[52] U.S. Cl. .................... 514/307; 546/23; 546/146; 546/147; 546/148; 546/150

[58] Field of Search ................ 546/23, 146, 147, 148, 546/150; 514/307

[56] References Cited

U.S. PATENT DOCUMENTS 4,746,653  5/1988  Hutchison et al. .................... 514/89
4,761,405  8/1988  Rzeszotarski et al. .............. 514/114

FOREIGN PATENT DOCUMENTS 129461A   6/1983  European Pat. Off. .
142740A  10/1983  European Pat. Off. .

OTHER PUBLICATIONS

Ksander et al; *J. Med. Chem.*, vol. 28, p. 1606 (1985).
Ito, *Chem. Pharm. Bull.*, vol. 16(3), p. 455 (1968).

*Primary Examiner*—Mary C. Lee
*Assistant Examiner*—Jacqueline Haley
*Attorney, Agent, or Firm*—Robert A. Conrad; Leroy Whitaker

[57] ABSTRACT

The present invention provides novel bicyclic derivatives useful as excitatory amino acid receptor antagonists and in treating a variety of associated nervous system disorders.

20 Claims, No Drawings

EXCITATORY AMINO ACID RECEPTOR ANTAGONISTS

SUMMARY OF THE INVENTION

The present invention provides compounds which are antagonists of excitatory amino acid receptors. More specifically, the present invention relates to a compound of the formula

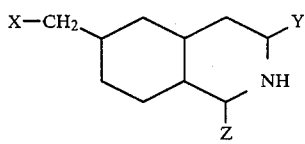

wherein:

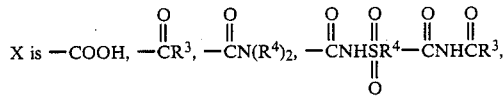

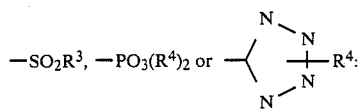

one of Y and Z is

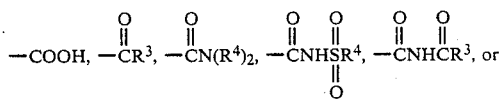

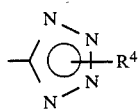

and the other of Y and Z is hydrogen;
each $R^3$ is independently $C_1$-$C_{16}$ alkoxy, phenyl-substituted $C_1$-$C_4$ alkoxy, or an oral ester forming group;
each $R^4$ is independently hydrogen, $C_1$-$C_{16}$ alkyl, phenyl-substituted $C_1$-$C_4$ alkyl, or phenyl; or
a pharmaceutically acceptable salt thereof.

The invention also provides pharmaceutical formulations comprising a compound of Formula I and a pharmaceutically acceptable carrier, diluent or excipient therefor.

Further embodiments of the invention include a method of blocking one or more excitatory amino acid receptors, as well as methods for treating a variety of disorders which have been linked to the excitatory amino acid receptors including neurological disorders (for example, epilepsy), stroke, anxiety, cerebral ischaemia, muscular spasms and neurodegenerative disorders such as Alzheimer's Disease and Huntington's Disease, employing a compound of Formula I.

DETAILED DESCRIPTION OF THE INVENTION

In the above formula, the term "$C_1$-$C_{16}$ alkyl" represents a straight or branched alkyl chain having from one to sixteen carbon atoms. Typical $C_1$-$C_{16}$ alkyl groups include methyl, ethyl, n-propyl, isopropyl, n-butyl, isobutyl, sec-butyl, t-butyl, n-pentyl, isopentyl, n-hexyl, 2-methylpentyl, n-octyl, decyl, undecyl, hexadecyl, and the like. The term "$C_1$-$C_{16}$ alkyl" includes within it the terms "$C_1$-$C_6$ alkyl" and "$C_1$-$C_4$ alkyl". The term "$C_1$-$C_{16}$ alkoxy" can be represented by ($C_1$-$C_{16}$ alkyl)—O— and includes within it the term "$C_1$-$C_4$ alkoxy".

The term "phenyl-substituted $C_1$-$C_{16}$ alkyl" represents a $C_1$-$C_{16}$ alkyl group bearing a phenyl group, such as benzyl, 1-phenylethyl, 2-phenylethyl, 3-phenylpropyl, 4-phenylbutyl, 2-methyl-2-phenylpropyl, and the like.

The term "oral ester forming group," as used herein, represents a substituent which, when attached to the carboxylic acid group, forms an ester function suitable for administration to mammals in need of treatment. Examples of such oral ester forming groups include $C_1$-$C_4$ alkoxy; benzyloxy; benzyloxy substituted on the phenyl ring with halogen, $C_1$-$C_4$ alkyl or $C_1$-$C_4$ alkoxy; $C_1$-$C_5$ alkanoyloxymethyl; or $C_1$-$C_5$ alkanoyloxymethyl substituted on the oxomethyl with $C_1$-$C_4$ alkyl or $C_4$-$C_7$ cycloalkyl.

While all the compounds of the present invention are believed to be antagonists of excitatory amino acid receptors, there are certain compounds of the invention which are preferred for such use. Preferably, the ring juncture is cis, Y is —COOH, Z is hydrogen, and X is —COOH, 5-tetrazolyl or phosphonyl, i.e., the compounds of Formula Ia wherein X' is —COOH, 5-tetrazolyl, or phosphonyl. Other preferred aspects of the present invention will be noted hereinafter.

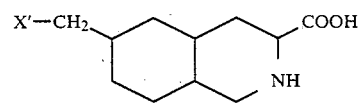

The compounds of the present invention possess four asymmetric carbon atoms represented by the substituted carbon atom adjacent to the ring NH group, the carbon atom where X—$CH_2$— is attached, and the two bridgehead carbon atoms. As such, the compounds can exist as diastereoisomers, each of which can exist as the racemic mixture of such isomers or each individual optical isomer. Accordingly, the compounds of the present invention will include not only the racemates, but also their respective optically active isomers.

As pointed out above, this invention includes the pharmaceutically acceptable salts of the compounds defined by Formula I. These salts can exist in conjunction with the acidic or basic portion of the molecule and can exist as acid addition, primary, secondary, tertiary or quaternary ammonium or alkali metal or alkali earth metal salts. Acids commonly employed to form such salts include inorganic acids such as hydrochloric, hydrobromic, hydroiodic, sulfuric and phosphoric acid, as well as organic acids such as paratoluenesulfonic, methanesulfonic, oxalic, para-bromophenylsulfonic, carbonic, succinic, citric, benzoic and acetic acid, and related inorganic and organic acids. Such pharmaceutically acceptable salts thus include sulfate, pyrosulfate, bisulfate, sulfite, bisulfite, phosphate, ammonium, monohydrogenphosphate, dihydrogenphosphate, metaphosphate, pyrophosphate, chloride, lithium bromide, iodide, acetate, magnesium, propionate, tetramethylammonium, decanoate, caprylate, acrylate, formate, isobutyrate, caprate, heptanoate, potassium, propiolate, oxalate, trimethylammonium, malonate, succinate, suberate, sebacate, fumarate, maleate, butyne-1,4-dioate, sodium, hexyne-1,6-dioate, benzoate, chlorobenzoate, methylbenzoate, dinitrobenzoate, hydroxybenzoate, methoxybenzoate, phthalate, sulfonate, methylammonium, xylenesulfonate, phenylacetate, phenylpropionate, phenylbutyrate, citrate, lactate, calcium, β-hydroxybutyrate, glycollate, maleate, tartrate, methanesulfonate, propanesulfonate, naphthalene-1-sulfonate, naphthalene-2-sulfonate, mandelate and the like salts.

Compounds of the present invention can contain one or two tetrazole rings. Tetrazole is known to exist as tautomeric structures. The tetrazole having the double bond on the nitrogen atom at the 1-position and the R substituent on the N-2 nitrogen atom is properly named as a 2H-tetrazole and is represented by the following structure:

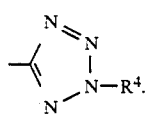

This compound has a corresponding tautomeric form wherein the R substituent is at N-1 with the double bond on the nitrogen atom of the 4-position. These compounds are named in part as 1H-tetrazoles and possess the following part structure:

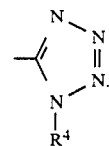

Mixtures of the two tautomers are referred to herein as 1(2)H-tetrazoles. The present invention contemplates both individual tautomeric forms as well as the combination of the two tautomers.

The compounds of the present invention may be prepared by procedures well known to those of ordinary skill in the art. Preferably, a hydroxy substituted 3-carbalkoxy-1,2,3,4-tetrahydroisoquinoline is blocked at the ring nitrogen with a standard blocking reagent and reduced to the corresponding fully saturated bicyclic ring system or a hydroxy substituted 1-carbalkoxy-1,2,3,4-tetrahydroisoquinoline is reduced to the corresponding fully saturated bicyclic ring system, then blocked at the ring nitrogen with a standard blocking reagent. The blocked hydroxy compound is oxidized to a ketone which is then reacted with a Wittig reagent to introduce a precursor group on the ring. Reduction of this functionality and further transformation results in compounds of Formula I. This reaction may be represented by the following scheme which is illustrative for compounds of Formula I wherein Z is hydrogen:

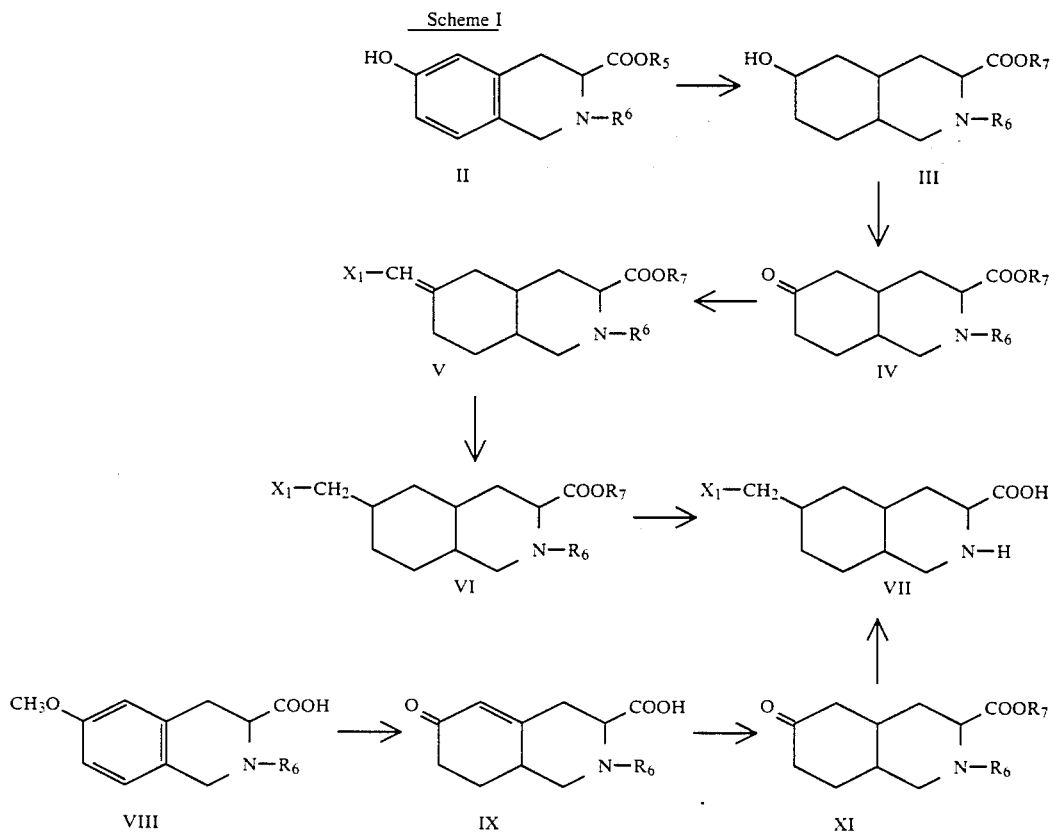

The hydroxy substituted carboxylic acid tetrahydroquinoline II ($R_5=R_6$=hydrogen) is converted to the corresponding ester derivative II ($R_5=C_1-C_4$ alkyl, $R_6$=H) according to standard esterification conditions. This intermediate is then protected with a blocking group, preferably a $C_1$–$C_6$ alkoxycarbonyl group, to provide the doubly protected intermediate II wherein $R_5$ is $C_1$–$C_4$ alkyl and $R_6$ is COO($C_1$–$C_6$ alkyl). This material is hydrogenated in the presence of a catalyst such as platinum oxide or rhodium on alumina and a suitable solvent. Suitable solvents include the alcohols, such as ethanol and especially methanol. The reaction is substantially complete after about one to about 24 hours when conducted at a temperature in the range of about 20° C. to about 100° C. The desired product III ($R_7$ is $C_1$–$C_4$ alkyl) is easily isolated by filtering the reaction mixture through diatomaceous diatonaceous earth and concentrating the filtrate under vacuum. The resulting residue may be further purified, if desired, but is preferably used directly in the following reaction.

The hydroxy intermediate III thus prepared is next oxidized to provide the corresponding ketone IV. This transformation can be accomplished by the use of any of a number of mild oxidizing agents, such as pyridinium chlorochromate, pyridinium dichromate, or oxalyl chloride and dimethylsulfoxide. As will be appreciated, the oxidizing agent and conditions employed should be sufficient to convert the secondary alcohol to the ketone without oxidizing other functionalities of the bicyclic ring system.

Intermediate IV is then reacted with a Wittig reagent of the general Formula $(CH_3CH_2O)_2POCH_2X_1$ wherein $X_1$ is $COOR_7$, CN, or $PO(OR^4)_2$. This reaction is generally accomplished by treating the appropriate diethylphosphonate with a strong base, such as sodium hydride, to generate the sodium salt of the phosphonate which is then reacted in a nonreactive solvent, such as dry tetrahydrofuran, with IV to provide the methylene derivative of Formula V. This reaction is generally carried out between 0° C. and the reflux temperature of the reaction mixture. When a slight molar excess of the phosphonate anion is employed, the reaction is generally complete after heating for about six hours at the reflux temperature of the mixture. Intermediate V is then reduced to provide the corresponding saturated analog. A preferred method of accomplishing this transformation is through catalytic hydrogenation, preferably in the presence of a catalyst such as palladium-on-carbon and an inert solvent such as ethanol.

The resulting intermediate VI can then be transformed into a compound of this invention by deblocking both the acid and nitrogen functionalities and also by converting the functional group $X_1$ to a functional group X. One versatile intermediate is the cyano derivative ($X_1 = -CN$) which can be used for preparing many of the other compounds of this invention.

For example, the cyano derivative VI ($X_1 = -CN$) be converted to a tetrazole intermediate and then to the compound of the invention according to the following process. The cyano starting material is reacted with tributyltin azide (also known as azido tributylstannane). This reaction is conducted at a temperature of about 50° C. to about 120° C., preferably at about 80° C., for about 12 to about 120 hours. The product may be isolated, but is preferably hydrolyzed directly to a compound of the invention by standard acid or base hydrolysis. The reaction is conducted at a temperature in the range of about 50° C. to about 150° C. for about 2 hours to about 24 hours and the product isolated. The product may then be purified by standard procedures such as crystallization with common solvents such as water, acetone or ethanol, or chromatography over solid supports such as silica gel, ion exchange resins or standard absorbents.

This reaction, when followed by acidic workup, not only effectively converts the nitrile intermediate to the desired tetrazole, but is also effective for removing the blocking groups $R_6$ and $R_7$.

Alternatively, the corresponding acid of this invention (VII, X = —COOH) can be prepared from the same nitrile intermediate simply by heating the nitrile with acid, preferably at the reflux temperature of the solution. Once again, this treatment effectively hydrolyzes not only the nitrile to the acid but also deblocks the $R_6$ and $R_7$ groups to provide the final compound of this invention.

Compounds of the invention wherein X, Y, or Z are other than the free carboxylic acid substituent are prepared by procedures well known to one of ordinary skill in the art. Compounds wherein X, Y, or Z are —C(=O)$R^3$ and $R^3$ is $C_1$–$C_{16}$ alkoxy or phenyl substituted $C_1$–$C_4$ alkoxy are prepared by esterification of the free carboxylic acid with an appropriate alcohol $R^3H$ in the presence of hydrogen chloride gas. The compounds wherein X, Y, or Z are —C(=O)$R^3$ and $R^3$ is an oral ester forming group are prepared by standard alkylation or acylation techniques. Compounds wherein X, Y, or Z are —C(=O)O(phenyl), —C(=O)N($R^4$)$_2$, —C(=O)NHSO$_2R^4$ or —C(=O)—NHC(=O)$R^3$ are prepared by the reaction of the free carboxylic acid derivative of the intermediate which is blocked with $R_6$ as defined above (either isolated as a partial hydrolysis product in the conversion of VI to VII or VII which has been converted into a N-$R_6$ blocked intermediate in the same manner as described above) with an appropriately substituted amine NH($R^4$)$_2$, sulfonamine NH$_2$SO$_2R^4$ or acylamine NH$_2$C(=O)$^3$ in the presence of a coupling reagent and mutual organic solvent. Suitable coupling reagents include the carbodiimides such as N,N'-dicyclohexylcarbodiimide, N,N'-diisopropylcarbodiimide, or N,N'-diethylcarbodiimide; the imidazoles such as carbonyldiimidazole; as well as reagents such as N-ethoxycarbonyl-2-ethoxy-1,2-dihydroquinoline (EEDQ). The resulting compound is then deblocked of the $R_6$ group as hereinbefore described. Compounds wherein X, Y, or Z are tetrazole or substituted tetrazole can also be prepared by hydrolyzing the cyano intermediate prepared as described above to the corresponding carboxylic acid derivative which is then treated with ammonia in the presence of a coupling reagent as described above to provide the corresponding primary carboxamide. The carboxamide is dehydrated to the corresponding carbonitrile upon treatment with phenylphosphinoyl dichloride or triphenylphosphine dibromide, in the presence of a tertiary amine such as triethylamine or pyridine. The resulting compound is converted to the tetrazole intermediate with tributyltin azide according to conditions hereinbefore described. The desired compound is then prepared as hereinbefore described.

Compounds of the present invention wherein the $R^4$ substituent on the tetrazole ring is other than hydrogen may also be prepared by known processes, or by processes analogous to such known procedures. Typically, alkylation of the unsubstituted starting material with an appropriate halide reagent $R^4$-Cl, $R^4$-Br, or $R^4$-I provides the desired compound of the invention or an intermediate which can be further modified to a compound of the invention as herein described. If a base is employed in the alkylation reaction, addition occurs first on the tetrazole ring if the other free nitrogen atoms are unsubstituted. Conducting the reaction in the absence of a base leads to preferential addition on the piperidine nitrogen atom. Any free nitrogen atom may also be blocked prior to the reaction, and deblocked subsequently according to standard conditions employing standard blocking reagents. Of course, di- or tri-substitution with the same substituent merely requires the use of an appropriate molar excess of reagent to account for each of the desired substituents on the final compound. As will be appreciated by those skilled in organic synthesis, the particular pattern of substitution, in the case where X and either Y or Z are both tetrazolyl, can be controlled by the use of blocking agents or introducing and functionalizing one tetrazolyl group before the other tetrazolyl group is introduced.

The preceding description of the synthesis of the compounds of the present invention prepares the preferred cis-ring juncture isomers. The diastereomers are easily separated from the mixture using standard chromatographic techniques, for example, employing silica gel or alumina adsorbents or fractional crystallization. An isolated diastereomer may be converted to the other diastereomer by treatment with a base such as a tertiary amine base or an alkali metal alkoxide in the corresponding alcohol. While separation or conversion may be conducted on any derivative in the foregoing synthetic scheme, preferably such separation or conversion is carried out on the blocked ketone intermediate as defined above.

The trans ring juncture isomers can be prepared in the following manner. Compound II is blocked at the phenolic hydroxy as the methyl ether by treatment with a base such as sodium or potassium carbonate and methyl iodide in a solvent such as acetone or DMF. The ester is then hydrolyzed with a base such as sodium or potassium hydroxide in water and/or ethanol to afford acid VIII. Treatment of the acid with lithium, sodium or potassium in liquid ammonia with or without added solvent such as ethanol, t-butanol, ether or tetrahydrofuran followed by aqueous acidic workup should afford the acid IX. Reduction of IX as for VIII should afford the ketone XI, having the trans ring juncture. Separation and interconversion of the axial and equitorial ester isomers should proceed as for IV. Conversion of the ketone XI to the corresponding products VII, having the trans ring juncture, should also proceed as described for the conversion of IV to VII.

The pharmaceutically acceptable salts of the invention are typically formed by reacting a compound of this invention with an equimolar or excess amount of salt forming reagent. The reactants are generally combined in a mutual solvent such as diethyl ether, benzene, ethanol or water and the salt normally precipitates out of solution within about one hour to 10 days, and can be isolated by filtration.

The hydroxy substituted intermediates corresponding to Formula II employed as starting materials in the synthesis of the compounds of this invention are known or can be prepared by procedures well known to those of ordinary skill in the art.

The following Examples further illustrate the compounds of the present invention and methods for their synthesis. The Examples are not intended to be limiting to the scope of the invention in any respect and should not be so construed.

EXAMPLE 1

Decahydro-6-[1(2)H-tetrazol-5-ylmethyl]-3isoquinolinecarboxylic acid

A. Preparation of 6-hydroxy-1,2,3,4-tetrahydro-3-isoquinolinecarboxylic acid hydrochloride To a mixture of 100.0 g of 3-hydroxyphenylalanine in 820 ml of 5% hydrochloric acid were added 78 ml of formaldehyde (37% in water). The reaction mixture was heated at 90°-95° C. (external bath temperature) for 45 minutes. The mixture was cooled and concentrated in vacuo. Five hundred milliliters of ethanol were added and the mixture was again concentrated in vacuo, affording 115 g of the title intermediate as a pale white solid, used without purification in the next step.

B. Preparation of ethyl 6-hydroxy-1,2,3,4-tetrahydro-3-isoquinolinecarboxylate hydrochloride To a mixture of 115 g of the acid from Example 1A above in 2.0 L of ethanol was bubbled hydrogen chloride gas for 10 minutes. Gas addition was ceased and the mixture heated to reflux overnight. The mixture was allowed to cool and the mixture concentrated in vacuo to provide 130 g of the desired subtitle intermediate which was used without further purification.

C. Preparation of ethyl 6-hydroxy-1,2,3,4-tetrahydro-2-methoxycarbonyl-3-isoquinolinecarboxylate The 130 g of ester from Example 1B above was suspended in 850 ml of methylene chloride. To this mixture were added 192 ml of diisopropylethylamine. The solution was cooled to 0° C. by means of an external ice bath and 42.6 ml of methyl chloroformate were added dropwise. After 30 minutes of stirring at 0° C., 60 ml of diisopropylethylamine were added and the mixture stirred an additional 30 minutes. One liter of 30% aqueous sodium hydrogen sulfate was added. The layers were separated and the aqueous layer extracted twice with methylene chloride and once with diethyl ether. All organic layers were combined and washed one time with a saturated sodium chloride solution. The organic solution was dried over magnesium sulfate, filtered, and concentrated in vacuo. The residue was purified by preparative HPLC to afford an oil. Trituration with ether afforded 86.2 g of the desired subtitled intermediate. A portion of this material was recrystallized from 2:1 ethyl acetate/hexane to provide purified material with a melting point of 124°-127° C.

D. Preparation of ethyl decahydro-6-hydroxy-2-methoxycarbonyl-3-isoquinolinecarboxylate A mixture of 85.8 g of the tetrahydroisoquinoline of Example 1C above in 900 ml of absolute ethanol was hydrogenated at 100° C. overnight in the presence of 22 g of 5% rhodium on aluminum oxide at 2000 p.s.i. The reaction mixture was filtered through Celite® and concentrated in vacuo. Ether was added and the mixture was filtered through Celite, then concentrated in vacuo, affording 87.9 g of the desired subtitled intermediate that was used without purification.

E. Preparation of ethyl decahydro-6-oxo-2-methoxycarbonyl-3-isoquinolinecarboxylate.

A mixture of 146.1 g of pyridinium chlorochromate, 146.1 g of powdered 4 Å sieves, and 1000 ml of methylene chloride was stirred for 1 hour at room temperature. A solution of 87.9 g of ethyl decahydro6-hydroxy-2-methoxycarbonyl-3-isoquinolinecarboxylate in 30 ml of methylene chloride was added dropwise in 200 ml of dichloromethane and the reaction mixture stirred for three hours at room temperature. Diethyl ether (1400 ml) was added to the mixture which was then filtered through a Celite® pad and silica gel pad. The filtrate was concentrated in vacuo, redissolved in diethyl ether, and again filtered through Celite and silica gel. Concentration of the filtrate afforded 78.4 g of the desired title product as a 28:72 mixture of equitorial: axial ester isomers. The residue was dissolved in 600 ml of ethanol, 1.11 g of sodium hydride dissolved in 60 ml of ethanol was added, and the mixture heated at 80° C. for 2.25 hours. The mixture was cooled and concentrated in vacuo. To the residue were added 700 ml of 1:1 dichloromethane/diethyl ether and this solution was washed with 300 ml of 10% aqueous sodium bisulfate. The organic layer was separated and the aqueous layer extracted three times with diethyl ether. The combined organic layers were dried over magnesium sulfate, filtered and concentrated in vacuo. The residue was filtered through silica gel with 40% ethyl acetate in hexane, and the filtrate was concentrated in vacuo to afford an oil. Crystallization from ether/hexane afforded 32.3 g of the desired subtitled intermediate, m.p. 79°–80° C., that was one compound by as determined by gas chromatography. By $^1$H NMR and X-ray crystallographic analysis, this ketone was determined to be ethyl 1a-R*-3-R*-4a-R*-decahydro-6-oxo-2-methoxycarbonyl-3-isoquinolinecarboxylate. It is assumed that this stereochemistry carries forward to each of the final products.

F. Preparation of ethyl decahydro-6-(cyanomethylene)-2-methoxycarbonyl-3-isoquinolinecarboxylate.

Sodium hydride (2.25 g of a 60% dispersion in oil) was thrice washed with hexane and suspended in 45 ml of dry tetrahydrofuran. With stirring, 10.0 g of diethyl cyanomethylphosphonate was added dropwise and the mixture allowed to stir under a nitrogen atmosphere for 30 minutes. To the phosphonate anion were added 11.5 g of ethyl decahydro-6-oxo-2-methoxycarbonyl-3-isoquinoline carboxylate in 60 ml of dry tetrahydrofuran. The mixture was heated for reflux for 0.5 hour, then cooled to room temperature and 50 ml of water and 50 ml of diethyl ether were added. The layers were separated and the aqueous layer extracted two times with diethyl ether. The combined organic layers were dried over magnesium sulfate, filtered, and concentrated in vacuo. The residue was purified by preparative HPLC to afford 12.1 g of the subtitle intermediate.

G. Preparation of ethyl decahydro-6-cyanomethyl-2-methoxycarbonylisoquinolinecarboxylate A mixture of 12.1 g of the intermediate from Example 1F above and 85 mL of absolute ethanol was hydrogenated overnight at room temperature in the presence of 2.5 g of 5% palladium-on-carbon. The reaction mixture was filtered and concentrated in vacuo. The residue was taken up in diethyl ether and filtered through Celited and the Celite washed twice with dichloromethane, then concentrated in vacuo. The residue was purified by preparative HPLC to afford 9.8 g of the desired product.

H. Preparation of decahydro-6-[1(2)H-tetrazole-5-ylmethyl]-3-isoquinolinecarboxylic acid A mixture of 9.6 g of the nitrile intermediate from Example 1G above was dissolved in 20.7 g of tributyltin azide and the mixture heated at 80° C. under a nitrogen atmosphere. After 3 days of heating, an additional 2 g of tributyltin azide was added and heating was continued for one more day. The mixture was cooled, dissolved in 200 mL of ether and then HCl gas was bubbled into the solution for 10 minutes. The mixture was concentrated in vacuo dissolved in 250 mL of acetonitrile and extracted five times with 200 mL each of hexane. The acetonitrile layer was concentrated in vacuo, then 500 mL of 6N hydrochloric acid was added and the mixture was heated to reflux overnight. The mixture was cooled, extracted three times with 100 mL each of ether, then the aqueous layer was concentrated in vacuo. The compound was dissolved in a minimum of water and placed on a Dowex 50X8-100 resin column eluting with water, 1:1 water/tetrahydrofuran, water, and 10% pyridine/water. The appropriate fractions were combined and concentrated in vacuo. The residue was suspended in acetone, refluxed for one hour filtered, and the solid washed with acetone and diethyl ether. After drying overnight at 60° C. under vacuum, 7.0 g of the desired title product was obtained, m.p. 200°–202° C. The elemental analysis was consistent for the product with 0.7 mol of water and 0.2 mol of acetone.

Analysis for $C_{12}H_{19}N_5O_2.0.25H_2O.0.2$ acetone $(C_3H_6O)$: Calc.: C, 52.28; H, 7.52; N, 24.19; Found: C, 52.09; H, 7.55; N, 24.20.

EXAMPLE 2

3-Carboxydecahydro-6-isoquinolineacetic acid hydrochloride

A mixture of 3.02 g of the nitrile intermediate from Example 1G above and 100 ml of 6N hydrochloric acid was heated at reflux in a nitrogen atmosphere overnight. The reaction was allowed to cool to room temperature and the mixture concentrated in vacuo. Acetone was added and the solution concentrated in vacuo. The resulting solid was suspended in diethyl ether, filtered, and the solid washed with acetone and diethyl ether affording 2.51 g of the desired title product, m.p. 263°–267° C. The elemental analysis was consistent for the product with 1.2 mol of ammonium chloride.

Analysis for $C_{12}H_{19}NO_4.HCl.1.2NH_4Cl$: Calc.: C, 42.15; H, 7.31; N, 9.01; Cl, 22.81; Found: C, 42.20; H, 7.46; N, 9.14; Cl, 22.67.

EXAMPLE 3

Decahydro-6-(phosphonomethyl)-3-isoquinoline-carboxylic acid

A. Preparation of ethyl decahydro-6-(diethylphosphonomethylene)-2-methoxycarbonyl-3-isoquinolinecarboxylate.

To a suspension of 2.4 g of 60% sodium hydride in oil, previously washed with hexane, in 50 ml tetrahydrofuran were added 17.3 g of methylene diphosphonic acid tetraethyl ester in 50 ml of tetrahydrofuran. After stirring for 15 minutes, 12.0 g of the ketone from Example 1E above were added as a solution in 35 ml of tetrahydrofuran. The reaction mixture was heated at reflux for 6 hours. After cooling, 200 ml of diethyl ether were added to the reaction mixture and the organic solution was washed twice with water. The combined aqueous layers were washed with diethyl ether. All of the organic layers were combined, washed with a saturated sodium chloride solution, dried, and filtered. After concentrating in vacuo, the residue was purified by high pressure liquid chromatography over silica gel. Combination and concentration of the appropriate fractions afforded 14.4 g of the desired subtitle intermediate.

B. Preparation of ethyl decahydro-6-(diethyl-phosphonomethyl)-2-methoxycarbonyl-3-isoquinolinecarboxylate The 14.4 g of intermediate from Example 3A above was hydrogenated following the procedure of Example 1G to provide 11.3 g of the title intermediate as a clear colorless oil.

C. Preparation of decahydro-6-(phosphonomethyl)-3-isoquinolinecarboxylic acid

The 11.3 g of intermediate from Example 3B above was heated at reflux overnight in 100 ml of 6N hydrochloric acid. The mixture was cooled and concentrated in vacuo. Twice acetone was added to the residue and removed under reduced pressure. The residue was dissolved in approximately 5 ml of water and treated with approximately 3.8 ml of propylene oxide at 50° C. for 30 minutes. After concentrating in vacuo, ethanol was added and the mixture heated at reflux. A white solid formed which, after cooling, was recovered by filtration. The residue was washed with ethanol, acetone, and diethyl ether. The solid was triturated with acetone, filtered, washing with acetone and ether and dried providing 7.2 grams of the title product, m.p. 208°–211° C. The elemental analysis corresponded to a product which had ½ mole of water and ¼ mole of acetone.

Analysis for $C_{11}H_{20}NO_5P.0.5H_2O.0.25C_3H_6O$: Calc.: C, 46.92; H, 7.54; N, 4.66; Found: C, 46.84; H, 7.36; N, 4.39.

EXAMPLE 4

Decahydro-6-(phosphonomethyl)-1-isoquinolinecarboxylic acid hydrochloride hemihydrate A. Preparation of ethyl 6-hydroxy-1,2,3,4-tetrahydro-2-t-butoxycarbonyl-1-isoquinoline carboxylate A mixture of 36.5 g of 3-(2-aminoethyl)phenol hydrobromide and 23.1 g of glyoxylic acid hydrate in 500 ml of 5% hydrochloric acid was stirred for 6.5 hours at 80° C. The solution was concentrated in vacuo and the residue dissolved in 1.2 L of ethanol which was then saturated with hydrogen chloride gas for 10 minutes. The mixture was heated at reflux overnight, then cooled and concentrated in vacuo. The resulting solid was dissolved in 400 ml of methylene chloride and 29 ml of Hunig's base followed by four 7.5 ml portions of di-t-butyldicarbonate over a one hour period. After approximately 45 minutes an additional 6 ml of Hunig's base were added. The mixture was washed with 500 ml of a 10% sodium bisulfate solution. The layers were separated and the aqueous layer extracted once with methylene chloride and once with diethyl ether. The organic layers were combined, dried, filtered, and concentrated in vacuo providing a red oil. High pressure liquid chromatography of the residue afforded 33.6 g of the subtitle intermediate which was used without further purification.

B. Preparation of ethyl 6-hydroxy-1,2,3,4-tetrahydro-1-isoquinoline carboxylate hydrochloride The 33.5 g of intermediate from Example 4A above were dissolved in a mixture of 200 ml of methylene chloride and 200 ml of trifluoroacetic acid. The solution was stirred at room temperature for two hours and then concentrated in vacuo. The residue was dissolved in approximately 300 ml of ethanol which had previously been saturated with hydrogen chloride gas. After concentration in vacuo, the material was suspended in diethyl ether and filtered. The resulting solid was recovered by filtration and dried to provide 25.8 g of the desired subtitled intermediate, m.p. 216°–218° C.

C. Preparation of ethyl decahydro-6-hydroxy-1-isoquinoline carboxylate hydrochloride The intermediate from Example 4B above (21.7 g) was hydrogenated in 370 ml of 6:1 ethanol/acetic acid at 60° C. with 10.8 g of 5% rhodium on carbon. After approximately 18 hours, an additional 10.8 g of catalyst was added and the hydrogenation continued an additional 21 hours. The reaction was filtered and the filtrate concentrated in vacuo. The residue was again hydrogenated under the same conditions in the presence of 21.6 g of catalyst. After four days, the reaction mixture was filtered and concentrated in vacuo providing 13.0 g of the desired subtitled intermediate which was used in the next step without purification.

D. Preparation of ethyl decahydro-6-hydroxy-2-t-butoxycarbonyl-1-isoquinoline carboxylate The 13.0 g of amine hydrochloride from Example 4C above were suspended in 150 ml of methylene chloride. Hunig's base (12.68 g) was added followed by 12.7 g of di-t-butyl dicarbonate. After stirring 60 minutes, the mixture was washed with a 10% solution of sodium bisulfate. The layers were separated and the aqueous layer extracted twice with methylene chloride and once with diethyl ether. The organic layers were combined, dried over magnesium sulfate, filtered and concentrated in vacuo to provide 16.4 g of the desired subtitled intermediate.

E. Preparation of ethyl decahydro-6-oxo-2-t-butoxycarbonyl-1-isoquinoline carboxylate Following the procedure of Example 1E above, the alcohol from Example 4D was treated with 23.7 g of pyridinium chlorochromate to provide after preparative HPLC 5.4 g of the desired subtitled intermediate. The material was dissolved in 130 mL of ethanol and treated with 1.65 mL of a solution of 600 mg of 60% sodium hydride in 15 mL of ethanol (to equilibrate the axial and equitorial ester isomers). After one hour at reflux, the mixture was concentrated in vacuo, dissolved in 200 mL of dichloromethane and washed with 100 mL of 10% aqueous sodium bisulfate. The aqueous layer was extracted with 100 mL of ether, then the combined organic extracts were washed with 100 mL of saturated aqueous sodium bicarbonate, dried over MgSO$_4$, filtered and concentrated in vacuo. Chromatography over silica gel provided 2.5 g of the title product as the equitorial isomer.

F. Preparation of ethyl decahydro-6-(diethylphosphonomethylene)-2-t-butoxycarbonyl-1-isoquinoline carboxylate Following the preparation of Example 3A above, 2.0 g of ethyl decahydro-6-oxo-2-t-butoxycarbonyl-1-isoquinoline carboxylate were treated with 2.6 g of methylene diphosphonic acid tetraethyl ester to provide 2.57 g of the desired subtitled intermediate.

G. Preparation of ethyl decahydro-6-(diethylphosphonomethyl)-2-t-butoxycarbonyl-1-isoquinoline carboxylate The methylene derivative of Example 4F above (2.36 g) was hydrogenated following the procedure of Example 1G to provide 2.13 g of the title intermediate.

H. Preparation of decahydro-6-(phosphonomethyl)-1-isoquinolinecarboxylic acid hydrochloride hemihydrate The title product was prepared in 76% yield from 1.8 g of the ester intermediate of Example 4G following the procedure of Example 3C, m.p. 231°–232° C.

Analysis for $C_{11}H_{20}NO_5P.0.85HCl.H_2O$: Calc.: C, 40.50; H, 7.06; N, 4.29; Cl, 9.24; Found: C, 40.61; H, 7.02; N, 4.45; Cl, 9.23.

EXAMPLE 5

Decahydro-6-(tetrazol-5-ylmethyl)-1-isoquinolinecarboxylic acid

The title product was prepared in 55% overall yield beginning with 2.47 g of ethyl decahydro-6-oxo-2-t-butoxycarbonyl-1-isoquinoline carboxylate following the procedures of Examples 1F, 1G, and 1H.

Analysis for $C_{12}H_{19}N_5O_2.0.75H_2O.0.10C_3H_6O$ (acetone): Calc.: C, 51.90; H, 7.47; N, 24.60; Found: C, 51.99; H, 7.35; N, 24.64.

EXAMPLE 6

Decahydro-6-(phosphonomethyl)-3-isoquinoline-carboxylic acid ethyl ester

A solution of 2.62 g of the amino acid of Example 3C above, which had ½ mole of water and ¼ mole of acetone as solvates, was suspended in 250 ml of ethanol. The solution was saturated with hydrogen chloride gas for 10 minutes, then the solution was heated at reflux overnight. After cooling and concentration in vacuo, the residue was dissolved in 15 ml of water and 2 mL of propylene oxide were added. After 1 hour at 50° C., the material was concentrated in vacuo, then dissolved in water and purified on a Dowex 50X8-100 resin column as in Example 1H to afford a foam. The foam was suspended in acetone and heated to reflux for 30 minutes, then cooled and filtered. The residue was washed with acetone and ether and then dried in vacuo at 60° C. to afford 1.95 g of the desired title product, m.p. 184°–185° C.

Analysis for $C_{13}H_{24}NO_5P.0.4H_2$: Calc.: C, 49.96; H, 8.00; N, 4.48; Found: C, 49.98; H, 7.84; N, 4.64.

EXAMPLE 7

Decahydro-6-(phosphonomethyl)-3-isoquinoline carboxylic acid butyl ester

The title product was prepared in 95% yield following the procedure of Example 6 from 1.06 g of the same starting amino acid and butanol, m.p.=161°–169° C.

Analysis for $C_{15}H_{28}NO_5P.0.7H_2O.0.7C_3H_7ClO$ (chloropropanol): Calc.: C, 49.83; H, 8.39; N, 3.40; Found: C, 49.47; H, 7.99; N, 3.79.

EXAMPLE 8

The title product was prepared following the procedure of Example 6 from 1.25 g of the amino acid from Example 3 in 250 mL of HCl saturated hexanol. The product was isolated by dissolving in about 50 mL of ethanol and adding ethyl acetate to precipitate the product. The resulting solid was filtered, suspended in acetone and refluxed for one hour, then cooled and filtered, washing with acetone and ether to afford 0.28 g of the title product, m.p.=149°–155° C.

Analysis for $C_{17}H_{32}NO_5P.1.0C_3H_7ClO$ (chloropropanol): Calc.: C, 52.68; H, 8.62; N, 3.07; Found: C, 52.39; H, 8.37; N, 3.40.

As noted above, the compounds of this invention are excitatory amino acid antagonists. Therefore, another embodiment of the present invention is a method of blocking one or more excitatory amino acid receptors in mammals which comprises administering to a mammal requiring decreased excitatory amino acid neurotransmission a pharmaceutically effective amount of a compound of the invention.

The term "pharmaceutically effective amount", as used herein, represents an amount of a compound of the invention which is capable of blocking one or more excitatory amino acid receptors. The particular dose of compound administered according to this invention will of course be determined by the particular circumstances surrounding the case, including the compound administered, the route of administration, the particular condition being treated, and similar considerations. The compounds can be administered by a variety of routes including the oral, rectal, transdermal, subcutaneous, intravenous, intramuscular or intranasal routes. A typical daily dose will contain from about 0.01 mg/kg to about 20 mg/kg of the active compound of this invention. Preferred daily doses will be about 0.05 to about 10 mg/kg, ideally about 0.1 to about 5 mg/kg.

A variety of physiologic functions have been shown to be subject to influence by excessive stimulation of excitatory amino acid neurotransmission. As such, the compounds of the present invention are believed to have the ability to treat a variety of disorders in mammals associated with this condition which include neurological disorders such as convulsive disorders for example, epilepsy; stroke; anxiety; cerebral ischaemia; muscular spasms; and neurodegenerative disorders such as Alzheimer's Disease and Huntington's Disease. Therefore, the present invention also provides methods of treating the above disorders at rates set forth above for excitatory amino acid receptors in mammals.

Experiments were performed to demonstrate inhibitory activity of compounds of this invention at the N-methyl-D-aspartate (NMDA) subtype of excitatory amino acid receptor in the rat in vivo.

Male or female neonatal (7 to 8 days old) Sprague-Dawley rats were removed from the dam and placed in plastic observation chambers that were maintained at 30°–32° C. All test drugs were dissolved in normal saline. Activation of NMDA receptors in these rats leads to a readily observable generalized motor seizure, characterized by an increase in motor activity followed by clonic-tonic movements of the forelimbs and hindlimbs, and the continued loss of righting ability. These seizures are not blocked by administration of a non-NMDA selective antagonist drug, but are readily blocked by NMDA selective compounds.

Animals were injected by the intraperitoneal route with the test drug (1 ml/100 g of body weight) and observed for a 30 minute period for seizure (potential agonist) activity. They were then injected with NMDA at a dose of 20 mg/kg body weight i.p. to test for antagonist activity. In control rats (normal saline administered) this dose of NMDA results in seizures in more than 95% of the animals. Rats were observed for seizures an additional 30 minute period following NMDA administration. Animals were rated as being positive or negative for the clear demonstration of tonic-clonic seizure activity with loss of righting ability. Observations of seizures induced by the test compound alone (agonist activity) or blockade of NMDA-induced seizures by the test compound (antagonist activity) were scored separately. Generally, five animals were used at each dose of compound. The entire range and intervals of the doses used was 200, 100, 50, 20, 10, 5, 2, and 1 mg/kg. Doses were decreased in a stepwise fashion in this range until at least 3 out of 5 animals exhibited seizures. The minimum effective dose (MED) was the lowest test dose which prevented NMDA-induced seizures in at least 3 out of 5 animals as reported in Table II.

TABLE II

Minimum Effective Dose of Compounds of Formula I Against Neonatal Rat Convulsions

| Compound of Example No. | MED (mg/kg) |
| --- | --- |
| 1 | 20 |
| 2 | 50 |
| 3 | 5 |
| 4 | 100 |
| 5 | 200 |
| 6 | 50 |
| 7 | 50 |
| 8 | 100 |

The compounds of the present invention are preferably formulated prior to administration. Therefore, yet another embodiment of the present invention is a pharmaceutical formulation comprising a compound of the invention and a pharmaceutically acceptable carrier, diluent or excipient therefor.

The present pharmaceutical formulations are prepared by known procedures using well known and readily available ingredients. In making the compositions of the present invention, the active ingredient will usually be mixed with a carrier, or diluted by a carrier, or enclosed within a carrier which may be in the form of a capsule, sachet, paper or other container. When the carrier serves as a diluent, it may be a solid, semisolid or liquid material which acts as a vehicle, excipient or medium for the active ingredient. Thus, the compositions can be in the form of tablets, pills, powders, lozenges, sachets, cachets, elixirs, suspensions, emulsions, solutions, syrups, aerosol (as a solid or in a liquid medium), ointments containing, for example, up to 10% by weight of the active compound, soft and hard gelatin capsules, suppositories, sterile injectable solutions and sterile packaged powders.

Some examples of suitable carriers, excipients, and diluents include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, water syrup, methyl cellulose, methyl and propylhydroxybenzoates, talc, magnesium stearate and mineral oil. The formulations can additionally include lubricating agents, wetting agents, emulsifying and suspending agents, preserving agents, sweetening agents or flavoring agents. The compositions of the invention may be formulated so as to provide quick, sustained or delayed release of the active ingredient after administration to the patient by employing procedures well known in the art.

The compositions are preferably formulated in a unit dosage form, each dosage containing from about 5 to about 500 mg, more usually about 25 to about 300 mg, of the active ingredient. The term "unit dosage form" refers to physically discrete units suitable as unitary dosages for human subjects and other mammals, each unit containing a predetermined quantity of active material calculated to produce the desired therapeutic effect, in association with a suitable pharmaceutical carrier.

The following formulation examples are illustrative only and are not intended to limit the scope of the invention in any way.

FORMULATION 1

Hard gelatin capsules are prepared using the following ingredients:

| | Quantity (mg/capsule) |
| --- | --- |
| decahydro-6-[1(2)H—tetrazol-5-yl-methyl]-3-isoquinolinecarboxylic acid | 250 |
| starch, dried | 200 |
| magnesium stearate | 10 |
| Total | 460 mg |

The above ingredients are mixed and filled into hard gelatin capsules in 460 mg quantities.

FORMULATION 2

A tablet is prepared using the ingredients below:

| | Quantity (mg/tablet) |
| --- | --- |
| 3-carboxydecahydro-6-isoquinolineacetic acid | 250 |
| cellulose, microcrystalline | 400 |
| silicon dioxide, fumed | 10 |
| stearic acid | 5 |
| Total | 665 mg |

The components are blended and compressed to form tablets each weighing 665 mg.

FORMULATION 3

An aerosol solution is prepared containing the following components:

|  | Weight % |
| --- | --- |
| decahydro-6-(phosphonomethyl)-3-isoquinoline-carboxylic acid | 0.25 |
| ethanol | 29.75 |
| Propellant 22 (chlorodifluoromethane) | 70.00 |
| Total | 100.00 |

The active compound is mixed with ethanol and the mixture added to a portion of the Propellant 22, cooled to −30° C. and transferred to a filling device. The required amount is then fed to a stainless steel container and diluted with the remainder of the propellant. The valve units are then fitted to the container.

FORMULATION 4

Tablets each containing 60 mg of active ingredient are made as follows:

| 3-carboxydecahydro-6-isoquinoline-acetic acid phenylsulfonamide | 60 mg |
| --- | --- |
| starch | 45 mg |
| microcrystalline cellulose | 35 mg |
| polyvinylpyrrolidone (as 10% solution in water) | 4 mg |
| sodium carboxymethyl starch | 4.5 mg |
| magnesium stearate | 0.5 mg |
| talc | 1 mg |
| Total | 150 mg |

The active ingredient, starch and cellulose are passed through a No. 45 mesh U.S. sieve and mixed thoroughly. The solution of polyvinylpyrrolidone is mixed with the resultant powders which are then passed through a No. 14 mesh U.S. sieve. The granules so produced are dried at 50° C. and passed through a No. 18 mesh U.S. sieve. The sodium carboxymethyl starch, magnesium stearate and talc, previously passed through a No. 60 mesh U.S. sieve, are then added to the granules which, after mixing, are compressed on a tablet machine to yield tablets each weighing 150 mg.

FORMULATION 5

Capsules each containing 80 mg medicament are made as follows:

| 5-(decahydro-6-phosphonomethylisoquinoline-3-yl)-1(2)H—tetrazole | 80 mg |
| --- | --- |
| starch | 59 mg |
| microcrystalline cellulose | 59 mg |
| magnesium stearate | 2 mg |
| Total | 200 mg |

The active ingredient, cellulose, starch and magnesium stearate are blended, passed through a No. 45 sieve, and filled into hard gelatin capsules in 200 mg quantities.

FORMULATION 6

Suppositories each containing 225 mg of active ingredient may be made as follows:

| 5-(decahydro-6-[1(2)H—tetrazol-5-yl)-methyl]-3-isoquinoline-3-yl)-1(2)H—tetrazole | 225 mg |
| --- | --- |
| saturated fatty acid glycerides | 2,000 mg |
| Total | 2,225 mg |

The active ingredient is passed through a No. 60 mesh U.S. sieve and suspended in the saturated fatty acid glycerides previously melted using the minimum heat necessary. The mixture is then poured into a suppository mold of nominal 2 g capacity and allowed to cool.

FORMULATION 7

Suspensions each containing 50 mg of medicament per 5 ml dose are made as follows:

| 2,2-dimethylpropanoyloxymethyl decahydro-6-phosphonomethyl-3-isoquinolinecarboxylate | 50 mg |
| --- | --- |
| sodium carboxymethyl cellulose | 50 mg |
| syrup | 1.25 ml |
| benzoic acid solution | 0.10 ml |
| flavor | q.v. |
| color | q.v. |
| purified water to total | 5 ml |

The medicament is passed through a No. 45 mesh U.S. sieve and mixed with the sodium carboxymethyl cellulose and syrup to form a smooth paste. The benzoic acid solution, flavor and color are diluted with some of the water and added, with stirring. Sufficient water is then added to produce the required volume.

FORMULATION 8

An intravenous formulation may be prepared as follows:

| decahydro-6-phosphonomethyl-3-isoquinolinecarboxylic acid methylsulfonamide | 100 mg |
| --- | --- |
| isotonic saline | 1000 ml |

The solution of the above ingredients is administered intravenously at a rate of 1 ml per minute to a subject in need of treatment.

I claim:

1. A compound of the formula I $$X-CH_2 \cdots \text{(decahydroisoquinoline ring with substituents Y, NH, Z)}$$

X is $-COOH$, $-\overset{O}{\underset{\|}{C}}R^3$, $-\overset{O}{\underset{\|}{C}}N(R^4)_2$, $-\overset{O}{\underset{\|}{C}}NHSR^4$, $-\overset{O}{\underset{\|}{C}}NH\overset{O}{\underset{\|}{C}}R^3$, $-SO_2R^3$, $-PO_3(R^4)_2$ or $$-\overset{\|}{\underset{O}{S}}$$

tetrazolyl-$R^4$;

one of Y and Z is

-continued $-COOH, -\overset{O}{\underset{\|}{C}}R^3, -\overset{O}{\underset{\|}{C}}N(R^4)_2, -\overset{O}{\underset{\|}{C}}NH\overset{O}{\underset{\|}{S}}R^4, -\overset{O}{\underset{\|}{C}}NH\overset{O}{\underset{\|}{C}}R^3$, or

[tetrazole ring structure with $R^4$]

and the other of Y and Z is hydrogen;

each $R^3$ is independently $C_1$–$C_{16}$ alkoxy, phenyl-substituted $C_1$–$C_4$ alkoxy, benzyloxy substituted on the phenyl ring with halogen, $C_1$–$C_4$ alkyl, or $C_1$–$C_4$ alkoxy, $C_1$–$C_5$ alkanoyloxymethyl, or $C_1$–$C_5$ alkanoyloxymethyl substituted on the oxymethyl with $C_1$–$C_4$ alkyl or $C_4$–$C_7$ cycloalkyl;

each $R^4$ is independently hydrogen, $C_1$–$C_{16}$ alkyl, phenyl-substituted $C_1$–$C_4$ alkyl, or phenyl; or a pharmaceutically acceptable salt thereof.

2. A compound of claim 1 wherein the ring juncture is cis.

3. A compound of claim 2 wherein Z is hydrogen.

4. A compound of claim 3 having the Formula Ia

[structure showing decahydroisoquinoline with X'—CH₂, COOH, NH]   Ia wherein X' is —COOH, tetrazolyl, or phosphonyl.

5. The compound of claim 4 which is decahydro-6-[1(2)H-tetrazol-5-ylmethyl-3-isoquinolinecarboxylic acid or a pharmaceutically acceptable salt thereof.

6. The compound of claim 4 which is 3-carboxydecahydro-6-isoquinolineacetic acid or a pharmaceutically acceptable salt thereof.

7. The compound of claim 4 which is decahydro-6-(phosphonomethyl)-3-isoquinolinecarboxylic acid or a pharmaceutically acceptable salt thereof.

8. A method of blocking one or more excitatory amino acid receptors in mammals which comprises administering to a mammal requiring decreased excitatory amino acid neurotransmission a pharmaceutically effective amount of a compound of claim 1.

9. A method of treating epilepsy in mammals comprising administering to the mammal in need of treatment from epilepsy an antiepileptic amount of a compound of claim 1.

10. A method of treating stroke in mammals comprising administration to a mammal requiring treatment from a stroke an antistroke amount of a compound of claim 1.

11. A method of treating anxiety in mammals comprising administration to a mammal requiring treatment from anxiety an antianxiety amount of a compound of claim 1.

12. A method of treating cerebral ischaemia in mammals comprising administration to a mammal requiring treatment from cerebral ischaemia an antiischaemic amount of a compound of claim 1.

13. A method of treating muscular spasms in mammals comprising administration to a mammal requiring treatment from muscular spasms an antispasmodic amount of a compound of claim 1.

14. A method of treating Alzheimer's disease in mammals comprising administration to a mammal requiring treatment from Alzheimer's Disease a pharmaceutically effective amount of a compound of claim 1.

15. A method of treating Huntington's Disease in mammals comprising administration to a mammal requiring treatment from Huntington's Disease a pharmaceutically effective amount of a compound of claim 1.

16. A pharmaceutical formulation comprising a compound of claim 1 and a pharmaceutically acceptable carrier, diluent or excipient therefor.

17. A pharmaceutical formulation comprising a compound of claim 4 and a pharmaceutically acceptable carrier, diluent or excipient therefor.

18. A formulation according to claim 17 wherein the compound is decahydro-6-[1(2)H-tetrazol-5-ylmethyl]-3-isoquinolinecarboxylic acid or a pharmaceutically acceptable salt thereof.

19. A formulation according to claim 17 wherein the compound is decahydro-6-[1(2)H-tetrazol-5-ylmethyl]-3-isoquinolinecarboxylic or a pharmaceutically acceptable salt thereof.

20. A formulation according to claim 17 wherein the compound is decahydro-6-(phosphonomethyl)-acceptable salt thereof.

* * * * *

UNITED STATES PATENT AND TRADEMARK OFFICE
CERTIFICATE OF CORRECTION

PATENT NO. : 4,902,695
DATED : February 20, 1990
INVENTOR(S) : Paul L. Ornstein

It is certified that error appears in the above-identified patent and that said Letters Patent is hereby corrected as shown below:

Column 1, line 25,

" $-SO_2R^3, -PO_3(R^4)_2$ or 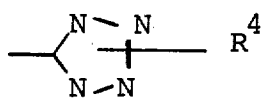 " should read

-- $-SO_2R^3, -PO_3(R^4)_2$ or  --.

Column 1, line 45, "$C_1-C_{16}$ alkyl" should read -- $C_1-C_{16}$ alkyl --.

Column 5, line 12, "diatomaceous diatonaceous earth" should read -- diatomaceous earth --.

Column 8, line 4, "3isoquinolinecarboxylic acid" should read -- 3-isoquinolinecarboxylic acid --.

Column 9, line 8, "decahydro6-hydroxy" should read -- decahydro-6-hydroxy --.

Column 10, line 1, "Celited" should read -- Celite® --.

Signed and Sealed this

Nineteenth Day of February, 1991

Attest:

HARRY F. MANBECK, JR.

Attesting Officer     Commissioner of Patents and Trademarks